United States Patent
Richter et al.

(10) Patent No.: US 9,880,254 B2
(45) Date of Patent: Jan. 30, 2018

(54) DETECTING A BLOOD SAMPLE

(71) Applicant: SANOFI-AVENTIS DEUTSCHLAND GMBH, Frankfurt am Main (DE)

(72) Inventors: Frank Richter, Tolz (DE); Ross MacArthur, Cheshire (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 71 days.

(21) Appl. No.: 14/240,800

(22) PCT Filed: Sep. 21, 2012

(86) PCT No.: PCT/EP2012/068698
§ 371 (c)(1),
(2) Date: Feb. 25, 2014

(87) PCT Pub. No.: WO2013/041704
PCT Pub. Date: Mar. 28, 2013

(65) Prior Publication Data
US 2014/0210979 A1    Jul. 31, 2014

(30) Foreign Application Priority Data
Sep. 22, 2011   (EP) .................................. 11182381

(51) Int. Cl.
*G01S 3/786* (2006.01)
*A61B 5/15* (2006.01)
(Continued)

(52) U.S. Cl.
CPC ............ *G01S 3/7864* (2013.01); *A61B 5/157* (2013.01); *A61B 5/150022* (2013.01);
(Continued)

(58) Field of Classification Search
CPC ....... A61B 5/1411; A61B 5/157; A61B 5/151; A61B 5/15146; A61B 5/14532;
(Continued)

(56) References Cited

U.S. PATENT DOCUMENTS

2003/0208140 A1* 11/2003 Pugh .................... A61B 5/1411
600/584
2008/0119884 A1* 5/2008 Flora .................... A61B 5/1411
606/182
(Continued)

FOREIGN PATENT DOCUMENTS

EP    1238632    9/2002
EP    1359418    11/2003
(Continued)

OTHER PUBLICATIONS

International Search Report for Int. App. No. PCT/EP2012/068698, dated Oct. 22, 2012.

*Primary Examiner* — Jamie Atala
*Assistant Examiner* — Ayman Abaza
(74) *Attorney, Agent, or Firm* — McDonnell Boehnen Hulbert & Berghoff LLP

(57) ABSTRACT

An apparatus for detecting presence of a blood sample is presented where the apparatus has a housing having an aperture that can receive a user's body part such that a camera in the housing can capture images of the user's body part. A processor, also in the housing, controls operation of the camera receive and determines from the captured images whether a predetermined quantity of blood is present on the surface of the user's body part.

12 Claims, 12 Drawing Sheets

(51) Int. Cl.
*A61B 5/151* (2006.01)
*A61B 5/157* (2006.01)

(52) U.S. Cl.
CPC ...... *A61B 5/15113* (2013.01); *A61B 5/15153* (2013.01); *A61B 5/15174* (2013.01); *A61B 5/150175* (2013.01); *A61B 5/150427* (2013.01); *A61B 5/150519* (2013.01); *A61B 5/15161* (2013.01); *A61B 5/150946* (2013.01)

(58) Field of Classification Search
CPC .......... A61B 5/15186; A61B 5/150022; A61B 5/150427; A61B 5/150519; A61B 5/15113; A61B 5/15174; A61B 5/150946; A61B 5/15161; C12Q 1/006; G01N 33/96; G01S 3/7864
USPC .......................................................... 348/77
See application file for complete search history.

(56) References Cited

U.S. PATENT DOCUMENTS

2008/0161725 A1* 7/2008 Wong .................. A61B 5/1411
  600/583
2011/0224515 A1 9/2011 Mir et al.
2012/0271197 A1* 10/2012 Castle ................. A61B 5/1411
  600/583

FOREIGN PATENT DOCUMENTS

WO 2005/104949 11/2005
WO 2006/031535 3/2006

* cited by examiner

DETECTING A BLOOD SAMPLE

CROSS REFERENCE TO RELATED APPLICATIONS

The present application is a U.S. National Phase Application pursuant to 35 U.S.C. § 371 of International Application No. PCT/EP2012/068698 filed Sep. 21, 2012, which claims priority to European Patent Application No. 11182381.1 filed Sep. 22, 2011. The entire disclosure contents of these applications are herewith incorporated by reference into the present application.

TECHNICAL FIELD

This invention relates to apparatus and method for detecting presence of a blood sample.

BACKGROUND

Diabetes sufferers may be provided with quantities of insulin, for instance by injection, sometimes a number of times daily. The quantity of insulin that is appropriate depends on the person's blood glucose level, so blood glucose level measurement can also occur a number of times daily.

Blood glucose level measurement typically is a multi stage process. The first is lancing, in which a lancet, or needle, is used to pierce the skin of a user, for example on the end or side of a finger. Once a suitable amount of blood has been produced, a sample is taken on a testing strip. A person may need to squeeze their finger in order to cause sufficient blood to be expelled. Sometimes lancing needs to be reperformed. The testing strip then is provided to a meter, typically an electronic meter, which analyses the sample, for example by determining a parameter (e.g. an electrochemical potential or voltage, resulting from a chemical reaction between the blood sample and an enzyme present in the testing strip, and provides a blood glucose measurement result. This measurement is then used to determine an amount of insulin to be consumed by the person.

Lancing can be painful or at least uncomfortable for a user. Numerous efforts have been made to reduce or minimise discomfort to a user in the lancing process. More effective efforts typically involve more complicated, and thus more expensive, mechanical or electro-mechanical arrangements.

SUMMARY

A first aspect of the invention provides apparatus for detecting presence of a blood sample, the apparatus comprising:
  a housing having an aperture, the aperture configured to receive a body part of a user;
  a camera having a field of view that encompasses at least a portion of the aperture, the camera configured to capture images of the user's body part; and
    a processor configured to:
    control operation of the camera;
    receive the captured images; and
    determine whether a predetermined quantity of blood is present on the surface of the user's body part.
The camera may be mounted on or within the housing. Alternatively, the camera may be mounted on or within the cartridge.

The housing may be configured to retain a cartridge containing at least one testing member. Each of the at least one testing members may be rotatably mounted on a shaft and may comprise a blood collection part located at a first position at the edge of the member.

The processor may be further configured, in response to a positive determination that a predetermined quantity of blood is present on the surface of the user's body part, to control the apparatus to present the blood collection part of a first one of the at least one testing members to the aperture.

Each of the at least one testing members may be movable along the cartridge such that different ones of the testing members are able to be presented at the aperture in turn.

The processor may be further configured to analyse the captured images to detect a position of the user's body part.

Each of the at least one testing members may comprise a lancet protruding from a second position at an edge of the member The processor may be further configured, in response to a detection that the user's body part is within a range of predetermined positions, to control the apparatus to advance the lancet of a first one of the at least one testing members into the aperture, thereby to lance the user's body part.

The processor may be further configured to analyse the captured images to monitor a position of the lancet.

The apparatus may further comprise a light source configured to illuminate the user's body part.

The processor may be further configured to analyse the captured images to measure a property of the blood sample.

The aperture may be configured such that a portion of the body part of the user enters the aperture.

The apparatus may further comprise a door which may cover the aperture when the door is closed. The door may be pivotable or slidable relative to the housing. The door may include an humidity seal.

Each of the at least one testing members may further comprise a cleaning portion that is arranged to contact the digit before lancing. The cleaning portion may also include a disinfecting portion. Additionally or alternatively, each of the at least one testing members may further comprise a cleaning portion that is arranged to contact the digit subsequent to lancing but prior to blood collection.

A second aspect of the invention provides a method of detecting presence of a blood sample, the method comprising:
  providing a housing having an aperture, the aperture configured to receive a body part of a user;
  providing a camera having a field of view that encompasses at least a portion of the aperture, the camera configured to capture images of the user's body part; and
    providing a processor configured to:
    control operation of the camera;
    receive the captured images; and
    determine whether a predetermined quantity of blood is present on the surface of the user's body part.

BRIEF DESCRIPTION OF THE DRAWINGS

Embodiments of the invention will now be described, by way of example only, with reference to the accompanying drawings, in which.

DETAILED DESCRIPTION

Figure 1:
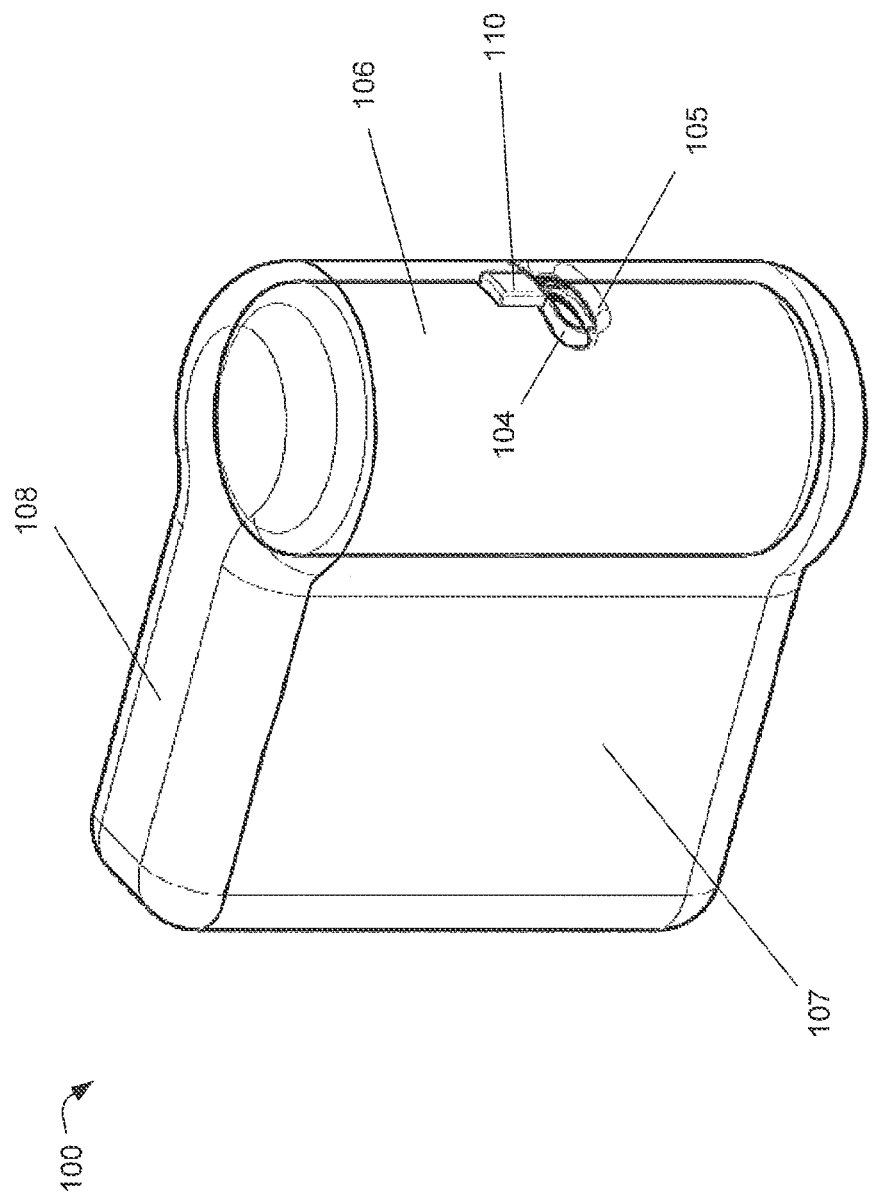
FIG. 1 is a wireframe perspective view of a blood glucose meter (BGM) according to aspects of the invention.
Figure 2:
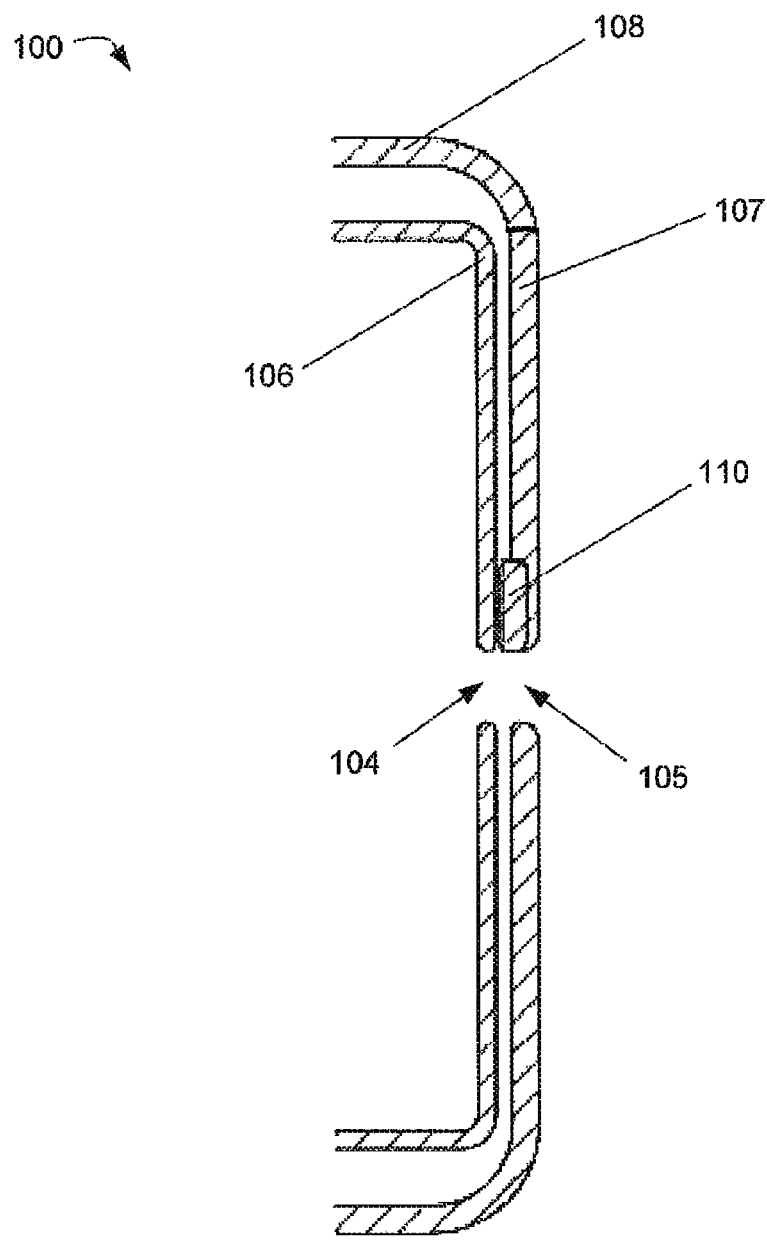
FIG. 2 is a cross-sectional view of a portion of the BGM of FIG. 1.

A blood glucose meter (BGM) 100 is shown in a perspective view in FIG. 1. FIG. 2 shows a cross-sectional view through the front face of the BGM 100. The BGM 100 has a generally flat base, is approximately as tall as it is long, and its width is approximately one-third of its height On one side face of the BGM may be provided with user inputs (not shown). These may take the form of push-switches or touch sensitive transducers, for instance. A display (not shown) may also be provided on the side of the BGM. This may take any suitable form, for instance a liquid crystal display (LCD), e-ink etc. In use, a user may control the BGM 100 using the inputs and may be provided with information by the BGM through the display.

Located at a front face of the BGM 100 is an aperture 105. The aperture 105 is located at approximately half of the height of the BGM. The aperture 105 is configured such as to be able to receive a part of a user's body, for the purpose of extracting a blood sample therefrom. For instance, the aperture 105 may be dimensioned so as to receive an end or a side part of a finger or thumb, or may be dimensioned so as to receive a side of a user's hand or a pinch of skin from a user's arm. The aperture may be rectangular in shape. Its edges may be beveled, so as to guide a user's digit into a specific location.

A corresponding aperture 104 is provided in the side of a cartridge 106. The cartridge has a generally cylindrical form, and is arranged vertically in the BGM 100.

In particular, the BGM includes an outer housing part 107. The outer housing part 107 forms at least the base, front, rear and side faces of the BGM 100. A lid part 108 may be attached to the first housing part 107. The lid part 108 may form the top surface of the BGM 100. The lid part 108 may be removed to allow access to the inside of the BGM 100. Alternatively, the lid part 108 may cover a smaller area above the cartridge 106 at the front face of the BGM 100. In this arrangement the outer housing 107 may extend to form the remainder of the upper surface and the lid part 108 may be removed to allow access to the cartridge 106 only.

A slidable or pivotable door (not shown) in the housing part 107 of the BGM 100 may hide the aperture 105 when the BGM is not in use such as to prevent the ingress of dirt and other potential contaminants into the aperture 105. This door may also act as or include an humidity seal to prevent reaction of enzymes contained within the testing strips from reacting with moisture in the air.

The cartridge 106 has a generally cylindrical form, and is arranged vertically. The cartridge 106 has a length that is between 3 or 4 times its diameter.

The lid part 108 is configured such that when it is in place on the BGM the cartridge 106 is retained by mechanical interaction between these components but is removable by a user. The exact way in which the lid part 108 is released from the BGM 100 is not critical and is not described in detail here.

The lid part 108 is configured such that when removed from the BGM 100 the cartridge 106 is able to be extracted from the BGM by moving it vertically along its axis. A replacement cartridge can then be introduced into the BGM 100 in the opposite manner to which the old cartridge 106 was removed. Once located at the bottom of the cavity in the BGM, the new cartridge 106 is surrounded by the first housing part 107. Once the lid part 108 has been replaced, to the position shown in FIG. 1, the cartridge 106 is retained in place by the action of the first housing part 107 and the lid part 108. The cartridge 106 and the cavity which receives the cartridge may have a keying feature, such as a protrusion and a groove, a non circular diameter, or the like. Thus, when the cartridge 106 is fully inserted, the cartridge aperture 104 is aligned with the aperture 105 in the outer housing 107.

A camera 110 is also shown in both of FIGS. 1 and 2. In the embodiment depicted, the camera 110 is disposed on the inner surface of the outer housing 107, immediately adjacent the aperture 105. The thickness of the wall of the outer housing 107 in this region may be reduced in order to accommodate the camera 110. Alternatively, the camera 110 may be mounted within a recess in the outer housing 107. In another alternative arrangement, the camera 110 may protrude from the outer housing 107. In any case, the camera 110 is arranged such that some or all of the aperture 105 is within the field of view of the camera 110.

In the embodiments depicted, then lens part of the camera 110 is immediately adjacent to the aperture 105. The camera may be focused on a point substantially in the centre of the aperture 105, or it may have a fixed focus point directed to the centre of the aperture 105. The camera lens is positioned with respect to the aperture 105 in the outer housing 107 such that the user's body part does not cover or otherwise obscure the lens when pressed against the aperture 105.

In some alternative embodiments, the camera 110 may be disposed on or within the body of the cartridge 106. The thickness of a wall of cartridge 106 in this region may be reduced in order to accommodate the camera 110. Alternatively, the camera 110 may be mounted within a recess in the cartridge wall. If the camera 110 is mounted on or within the cartridge 106, the camera may be angled towards the aperture 105 however the skilled person will be aware of other means of ensuring that the field of view of the camera 110 encompasses the aperture 105, such as by the use of lenses or mirrors. If the camera 110 is disposed on or within the cartridge 106, the cartridge also has contacts which communicate with corresponding contacts within the main body of the BGM 100 in order to supply power and signals to the camera 110 and to receive image data from the camera 110.

The camera 110 may be in communication with a processor, described in more detail below with reference to FIG. 3. The camera 110 is configured to capture images and relay them to the processor. The camera 110 may also comprise a light source to illuminate the aperture 105. Alternatively the light source may be a separate module provided within the body of the BGM 100.

Figure 3:
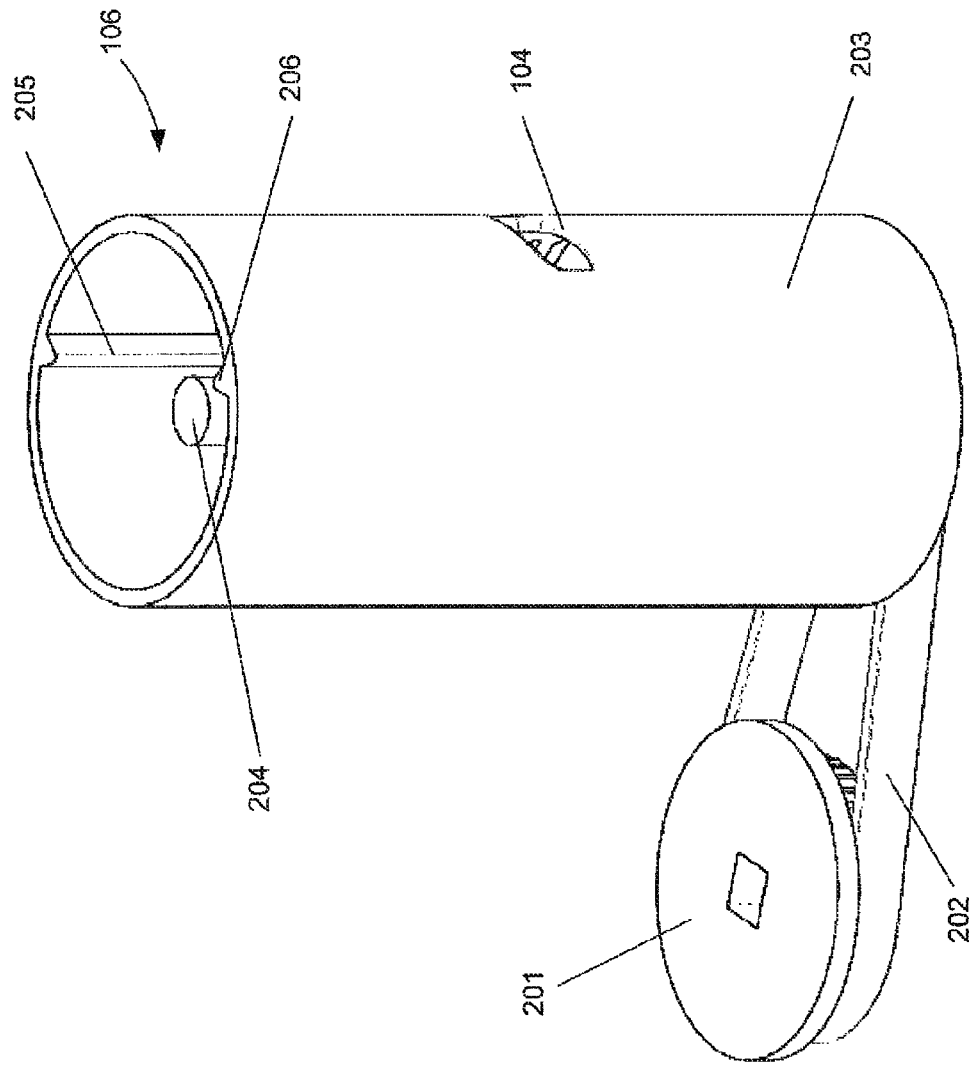
FIG. 3 illustrates components of embodiments of the BGM of FIG. 1.

FIG. 3 shows a subsystem 200 of the blood glucose meter 100. The subsystem 200 includes the cartridge 106, a drive wheel 201 and a drive belt 202.

In FIG. 3, the cartridge 106 is shown as having a hollow cylindrical housing part 203. An aperture 104 is formed in the hollow cylindrical housing part 203. Coaxial with the hollow cylindrical part 203 is an elongate shaft 204, only the top part of which is illustrated in FIG. 3. The length of the shaft 204 is such that its uppermost end is slightly below the uppermost end of the hollow cylindrical housing part 203. As will be described below, the shaft 204 is mechanically coupled with the drive belt 202 so as to be rotatable by rotation of the drive wheel 201.

Formed with the inner surface of the hollow cylindrical housing part 203 are first and second guide members 205, 206. In FIG. 3, it can be seen that the first and second guide members 205, 206 have a generally triangular cross section. One side of the triangular cross section of the first and second guide members 205, 206 is integral with the inner surface of the hollow cylindrical housing part 203, with a point of the triangular cross section extending towards the centre of the cartridge 106. A part of the length of the first guide member 205 is visible in FIG. 3, but only the uppermost surface of the second guide member 206 is visible in that figure.

Figure 4:
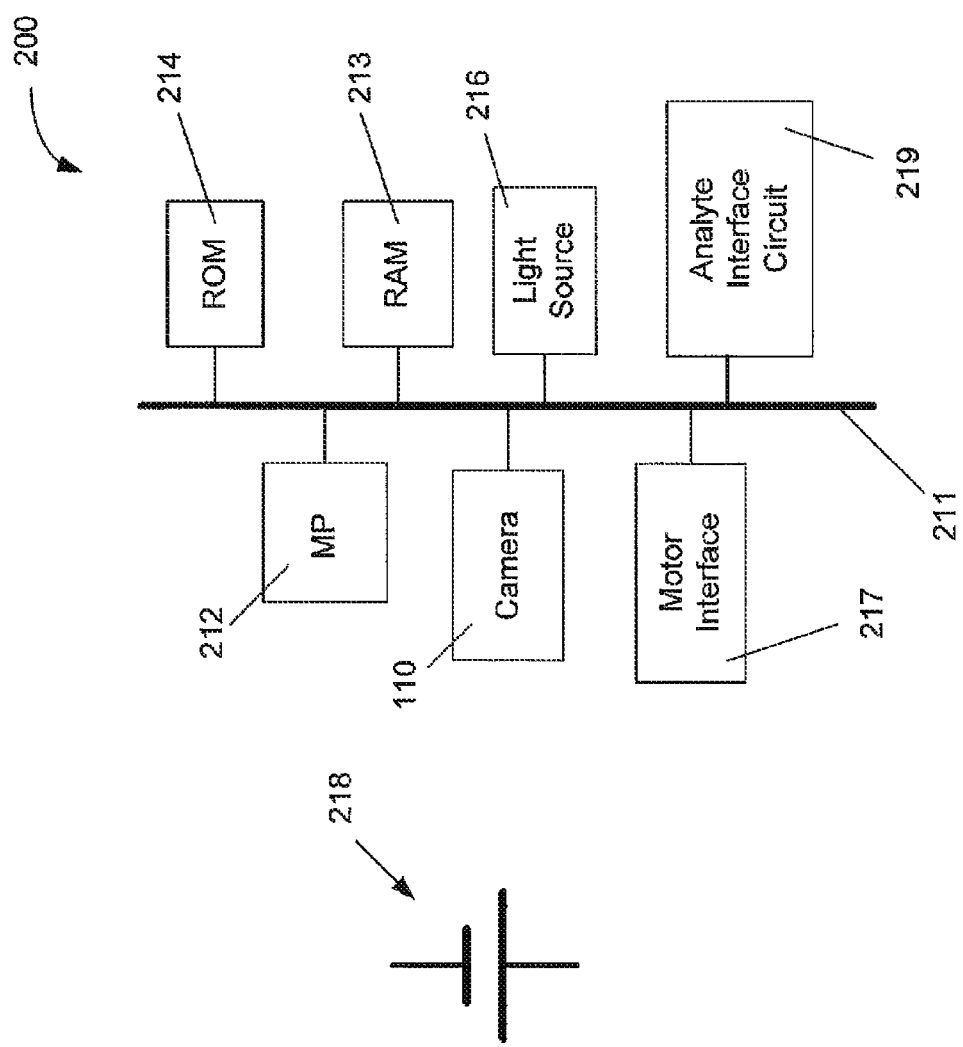
FIG. 4 is a schematic diagram of electrical components of the BGM of FIG. 1.

FIG. 4 shows some electronic components that form parts of the blood glucose meter 100. These components are provided within the housing 107.

A bus 211 is arranged to connect a number of components including a microprocessor 212, random access memory (RAM) 213, read-only memory (ROM) 214, a camera 110, a light source 216, an analyte interface circuit 219 and a motor interface 217. All of these components are powered by a battery 218, which may take any suitable form.

Stored in the ROM 214 is software and firmware that governs operation of the blood glucose meter 100. The software/firmware is executed by the microprocessor 212 using the RAM 213. The software/firmware stored in the ROM 214 is operable to operate the blood glucose meter 100 such as to allow control by a user through keys or input devices (if present). The software/firmware is also operable to control operation of the camera 110 and light source 116, to receive image data from the camera 110 and to process the received image data. A blood glucose measurement and other information may be provided on a display (if present) at suitable times by operation of the software/firmware and the microprocessor 212. The BGM 100 may also contain a display driver and user inputs interface (not shown).

The camera 110 may comprise any image sensing technology such as a charge-coupled device (CCD) or an active pixel sensor such as a complementary metal oxide semiconductor (CMOS) device. The camera 100 may have a fixed focal point or the focusing of the camera 110 may be adjustable. The camera focus may be adjusted automatically under control of the microprocessor 212. The light source 216 may comprise any suitable technology, such as an incandescent bulb, fluorescent bulb or LED. The light source may produce white light or coloured light. The light source 216 may be integral with the camera 110 and may be located immediately adjacent to the camera lens. Alternatively, the light source 216 may be a separate component located adjacent to the camera lens. In other alternatives, the light source 216 may be located on the opposite side of the aperture 105 from the camera 110. In embodiments where the camera is disposed on or within the housing of the cartridge 106, the light source may also be disposed on the cartridge 106 or may be disposed on the outer housing 107. In any case, the light source 216 is directed at or across the aperture 105 so as to illuminate a user's body part placed against the aperture 105. As the cartridge 106 is disposable, the camera 110 and/or light source 216, if disposed on the cartridge 106, are also disposable.

In further embodiments the BGM 100 may comprise multiple light sources 216 in order to provide greater or more uniform illumination of the user's body part.

The motor interface 217 allows the microprocessor 212, according to the software/firmware stored in the ROM 214, to control the motor that is coupled to the drive wheel 201, and any other motors that are included in the blood glucose meter 100.

Figure 6:
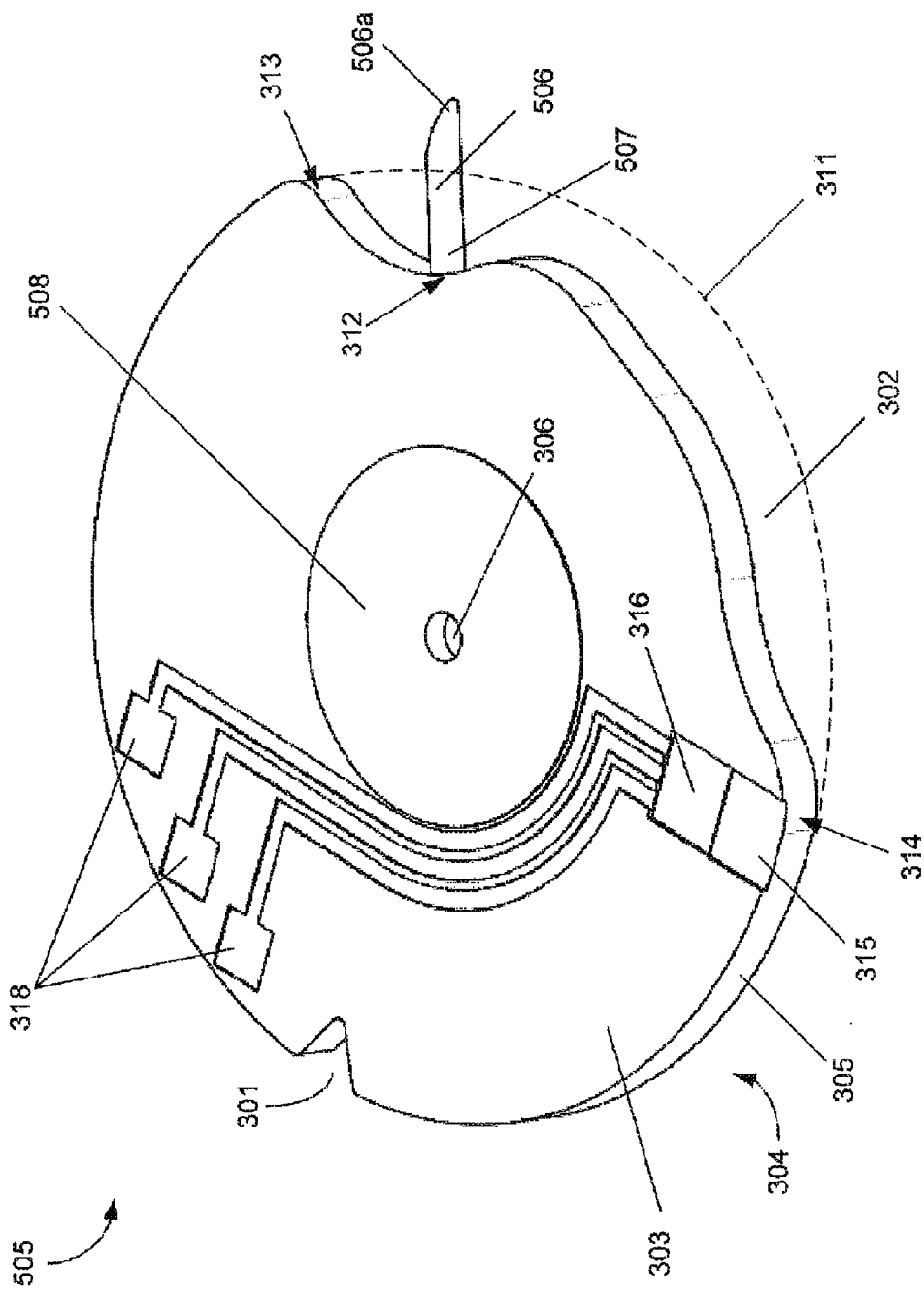
FIG. 6 illustrates a test disc member forming part of the FIG. 5 embodiment.

The analyte interface circuit 219 is operable to provide electrical signals with certain voltages to electrical contact terminals 401 (described in more detail with respect to FIG. 11), and thus via contact pads 318 to an analyte measuring part 316 (described in more detail with respect to FIG. 6). The analyte interface circuit 219 is also operable to measure parameters of signals such as to allow the microprocessor 212 to measure a blood glucose level of a blood sample.

Referring now to FIGS. 5 to 10, an arrangement embodying aspects of the invention is shown.

Figure 5:
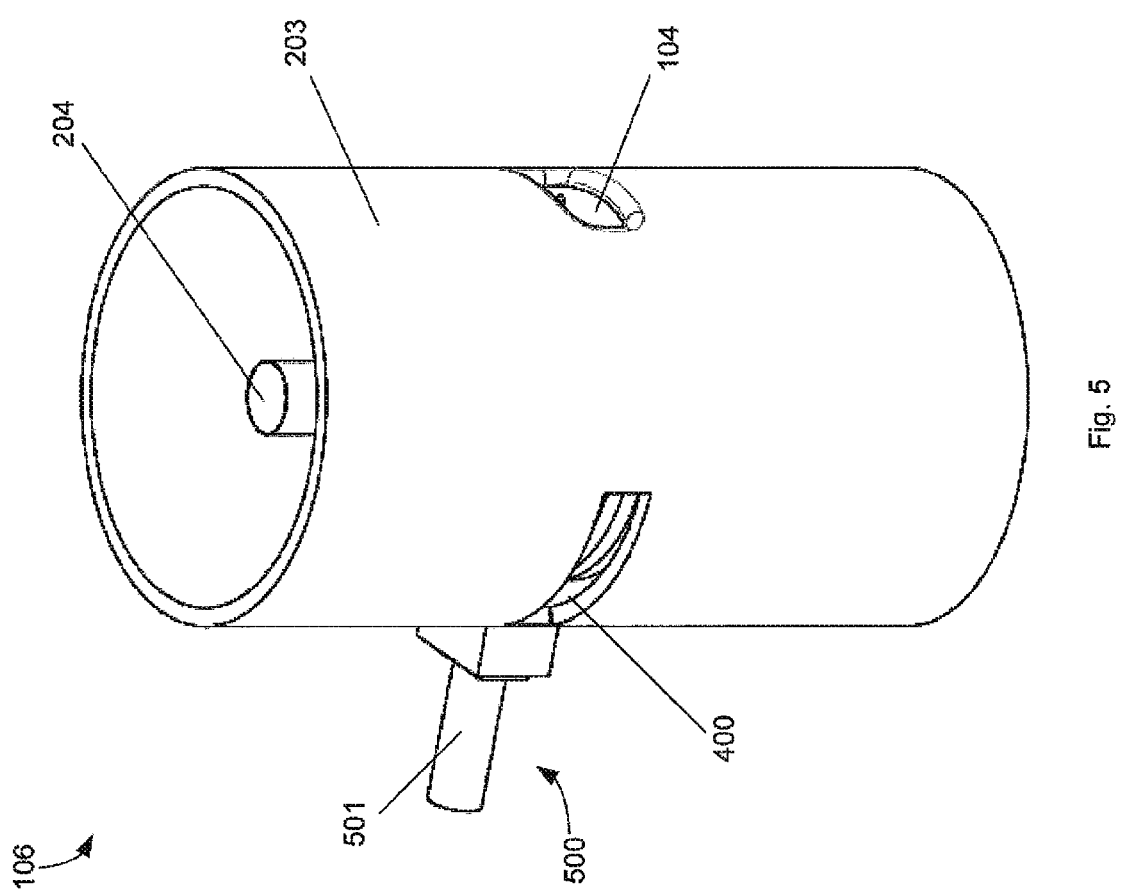
FIG. 5 illustrates components of the BGM of FIG. 1 in a perspective view.
Figure 11:
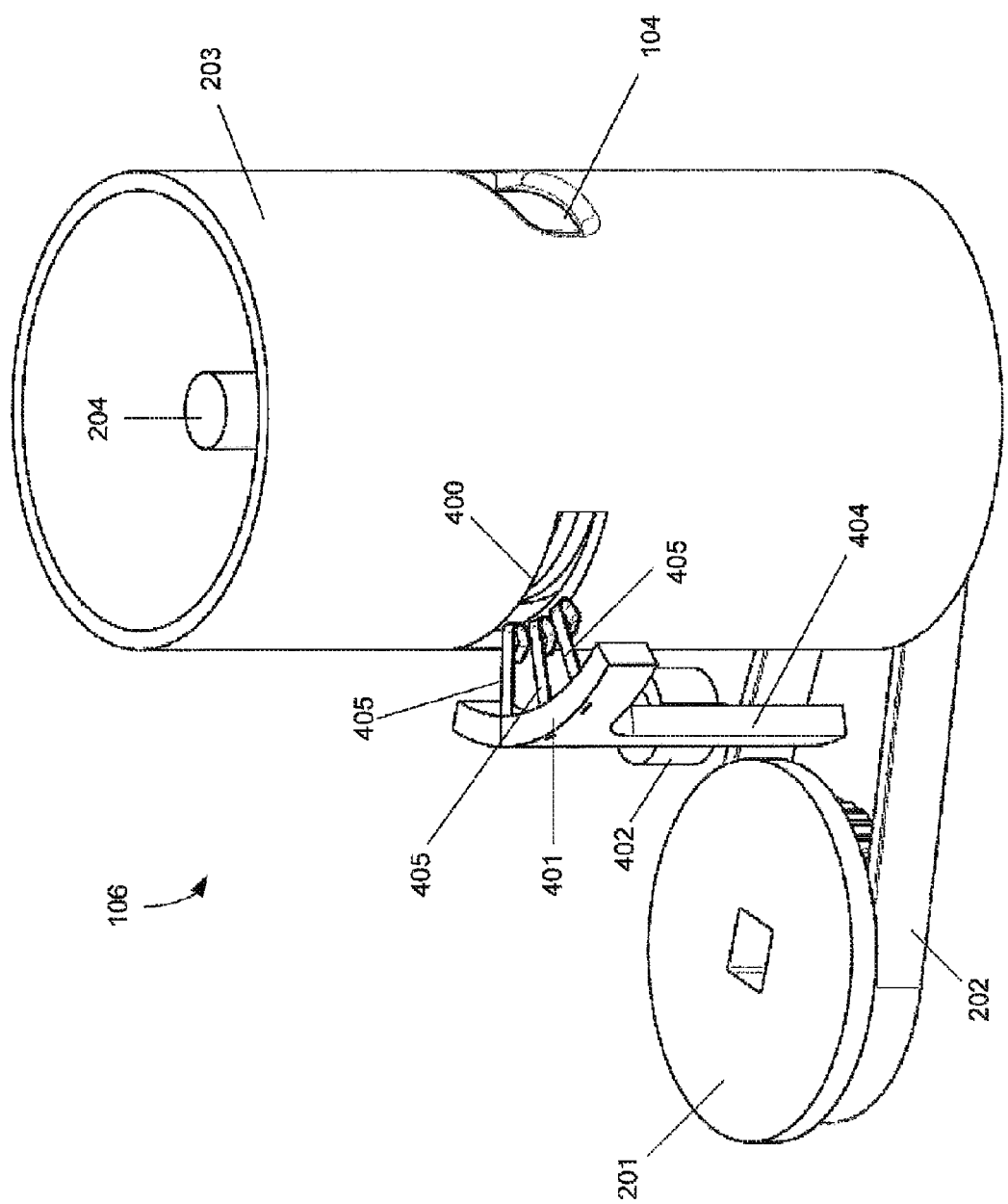
FIG. 11 is a perspective view of components of the BGM of FIG. 1.

As shown in FIG. 5, the hollow cylindrical housing part 203 is provided with the aperture 104 and a slit aperture 400 (described in greater detail with respect to FIG. 11). The shaft 204 is supported centrally within the hollow cylindrical housing part 203 of the cartridge 106.

A plunger arrangement 500 comprising a plunging arm 501 and a plunging head 502 is provided adjacent a plunging aperture (not shown) in the hollow cylindrical housing part 203. The plunging aperture (not shown) is located next to the slit aperture 400. The plunging aperture (not shown) is located directly opposite to the aperture 104. The plunger aperture and the slit aperture 400 may be combined to form a single aperture. The plunger aperture is configured to allow the plunging head 502 to be forced by the plunging arm 501 to a position internal to the hollow cylindrical housing part 203.

Within the cartridge 106 are plural test disc members, one of which is shown as 505 in FIG. 6. The test disc member 505 has a generally circular shape, although on one side a notch 301 is formed and on another side a cutaway portion 302 is provided.

The test disc member 505 includes an uppermost surface 303, a lowermost surface 304 and a disc edge 305. The diameter of the test disc member 505 is between 15 and 25 millimeters, for instance 20 millimeters. The thickness of the disc, which is equal to the height of the disc edge 305, is between 0.5 millimeters and 1 millimeter.

A hole 306 is formed at the centre of the test disc member 208. This hole 306 allows the test disc member 505 to be mounted on the shaft 204.

The underside of each test disc member 505 may be provided with a spacer member. The spacer member may comprise a slice of a hollow cylinder, for example. The height of the spacer member may be between 0.5 and 1 millimeter. When plural test disc members are stacked together, the spacer member provides separation between the upper surface 303 of one test disc member and the lower surface 304 of the test disc member that is directly above it. The separation is determined by the height of the spacer member.

A lancet 506 is provided extending from the disc edge 305 in the cutaway portion 302. A first end of the lancet 506 is embedded within the material of the test disc member 505, and a second end 506a is provided with a sharp point and extends outwardly. In particular, the lancet 506 extends in a radial direction with respect to the centre of the test disc member 505. The second end 506a of the lancet 506 is located at or just outside a circumference 311 of the test disc member 505. The circumference 311 is shown as a dotted line in FIG. 6 because it is virtual, instead of tangible. The lancet 506 extends from the disc edge 305 at a first position 312 on the disc edge. The first position 312 is close to a second position 313 at which the cutaway portion 302 starts. The cutaway portion 302 ends at a third position 314. Between the second and third positions 313, 314 opposite to the cutaway portion 302, the disc edge 305 generally takes the form of a circle, although the notch 301 interrupts that circle.

Located next to the third position 314 is a blood collection part 315. This may take any suitable form. For instance, it may comprise a laminated material. The blood collection part 315 has the function of drawing blood that is in contact with the disc edge 305 at the third position into the test disc member 505 to an blood analyte measuring part 316, that adjoins the blood collection part 315, for example a part containing an enzyme for blood glucose measuring, or the like. Blood may be drawn through capillary action. The analyte measuring part 316 includes an enzyme that reacts chemically with blood in such a way that blood glucose level can be measured. The analyte measuring part 316 is connected to first to third contact pads 318 by first to third conductive tracks 317. The contact pads 318 and the conductive tracks 317 are formed on the upper surface 303 of the test disc member 505. The analyte measuring part also is formed on the upper surface 303 of the test disc member 208. Some or all of the conductive tracks 317, the contact pads 318 and the analyte measuring part 316 may be printed onto the upper surface 303 of the test disc member 208.

Although in the figures three conductive tracks 317 and three conductive pads 318 are shown, it will be appreciated that this is merely illustrative. There may instead be only two conductive tracks 317 and two conductive pads 318, or alternatively there may be more than three conductive tracks and conductive pads.

The majority of the test disc member 505 may be substantially rigid. Alternatively, the majority of the test disc member 505 may have some degree of compressibility. However, an annular centre portion 508 is comprised of an elastically deformable material. In particular, the annular centre position 508 is deformable in the presence of an externally applied force. This means that the test disc member 505 can be displaced relative to the shaft 204, as will be described in more detail below. The material used to form the annular centre portion 508 may take any suitable form, and for instance may be a rubberised plastic.

The plural test disc members are biased in an upwards direction by bias means (not shown), which may be a spring. However, the test disc members are prevented from moving upwards within the cartridge 106 by virtue of the contact between the upper surface 303 of the uppermost test member and the lowermost end of the first guide member 205. Only when the notch 301 in the test disc member is aligned with the second guide member 206 is the test disc member free to move upwards.

Figure 7:
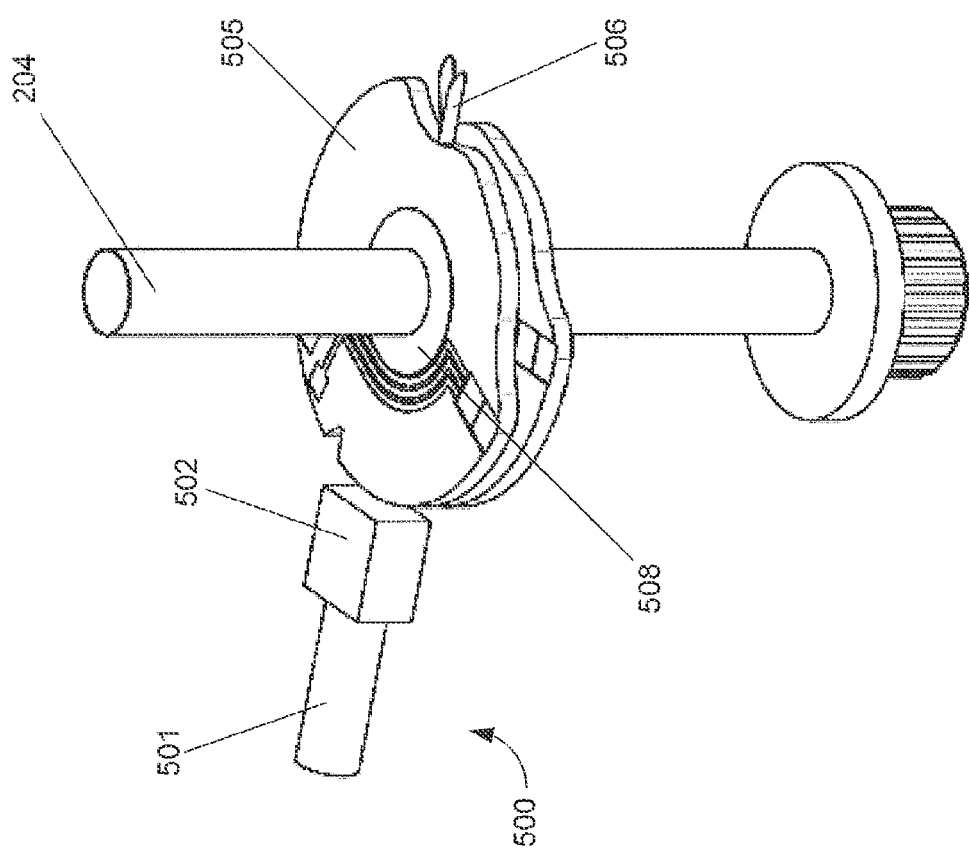
FIGS. 7 to 10 illustrate the embodiment of the BGM of FIG. 5 at different phases of operation.

In FIG. 7, the hollow cylindrical housing part 203 is omitted from the figure. In FIG. 7, the test disc member 505 is shown as having been rotated to a position at which the lancet 506 is coincident with the aperture 104. In use, a user places a body part (hereafter the part will be referred to as a user's digit, for the sake of convenience) against the aperture 105 in the outer housing 107. It can be seen that the plunging head 502 is aligned with the test disc member 505 such that movement of the plunger arrangement 500 along the longitudinal axis of the plunging arm 501 causes the plunging head to contact the test disc member 505 and apply force to it. Since the longitudinal axis of the plunging arm 501 is radial with respect to the shaft 204, the force applied by the plunger arrangement is directed towards the shaft 204.

Figure 8:
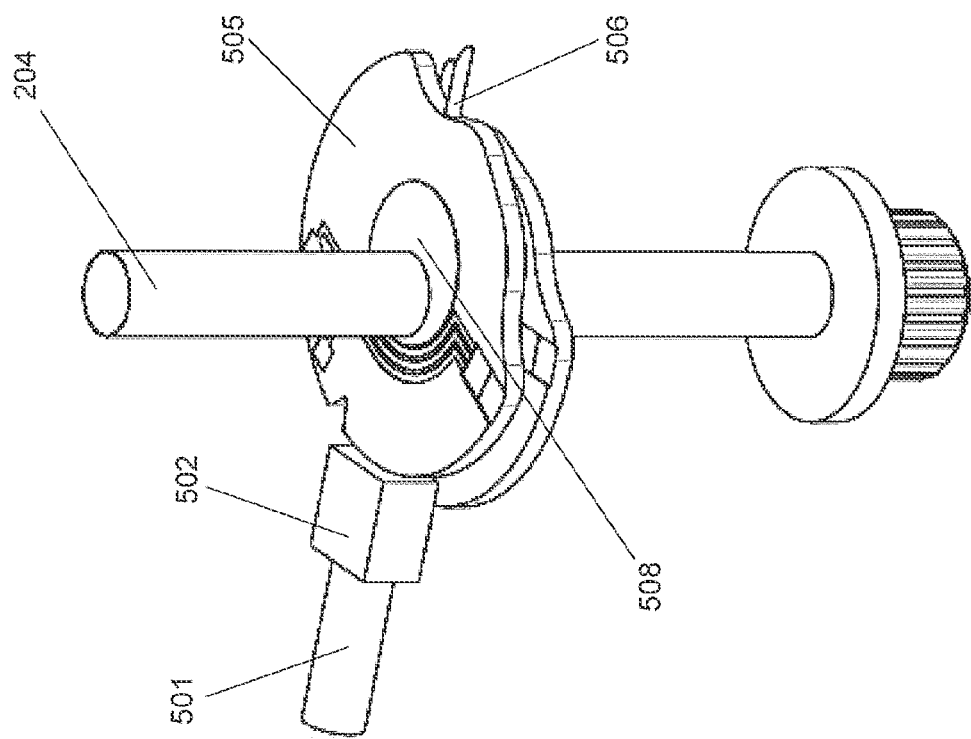

In FIG. 8, the arrangement is shown after a force has been applied to the plunger arrangement 500 so as to displace it by a predetermined amount. Here, the plunging head 502 has contacted the test disc member 505 on the opposite side of the test disc member to the lancet 506. The annular centre portion 508 has become compressed on the side closest to the plunger arrangement 500 such as to allow the whole of the test disc member 505 to be displaced in the direction of the force supplied by the plunger arrangement 500. The test disc member 505 remains horizontal by virtue of the spacer members 308.

Displacement of the test disc member 505 in the direction of the force supplied by the plunger arrangement 500 has resulted in displacement of the lancet 506 in a radial direction away from the shaft 204. In this position, the lancet 506 extends through the cartridge aperture 104 and the aperture 105 in the outer housing 107 such that the lancet penetrates the skin of the user's digit. This produces a puncture in the skin of the digit, through which blood can escape. This position is shown in FIG. 8. Removal of the force by the plunger arrangement 500 allows the annular centre portion 508 to return to its original form, through elastic reformation. After the plunger arrangement 500 has been fully retracted, the arrangement again has the form shown in FIG. 7. Here, the test disc member 505 is in its original position and the lancet 506 is retracted from the user's digit. It will be appreciated that it is the elasticity of the annular centre portion 508 of the test disc member 505 that allows the test disc member 505 to return to this position once the force applied through the plunger arrangement 500 is removed.

Referring again to FIG. 4, once the lancing of the user's digit has been performed, the camera 110 and light source 216 may be activated under control of the microprocessor 212. The field of view of the camera 110 encompasses the aperture 105 in the outer housing 107 in which the user has located their digit. The user's digit may obscure the majority of the light which would otherwise enter through the aperture 105. The light source 216 provides illumination of the user's digit to allow the camera 110 to capture clear images.

The microprocessor 212 is configured to receive image data from the camera 110 and to process the image data. The microprocessor 212 may process the image data to determine the quantity of blood which has been expelled from the puncture wound made by the lancing. The blood generally exits the puncture wound and forms a substantially circular droplet on the surface of the user's digit. The microprocessor 212 may use known information relating to the size of the aperture 105, distance of the camera 110 from the centre of the aperture 105 and the focal properties of the camera 110 to calculate the dimensions of the blood droplet from the received images and hence estimate the quantity of blood present. Alternatively or additionally, the microprocessor 212 may perform a colour analysis of the received images to determine when sufficient 'red blood' is present. It can be important that a sufficient blood sample is collected for analysis as the accuracy of the blood glucose measurement may be negatively affected if the blood sample collected is too small. The microprocessor 212 may make regular (e.g. one per second or fraction of a second) calculations of the quantity of blood expressed from the wound. When the microprocessor 212 detects that a predetermined quantity of blood has been expressed, it may control the motor via motor interface 217 to rotate the test disc member 505 to the blood collection position.

Figure 9:
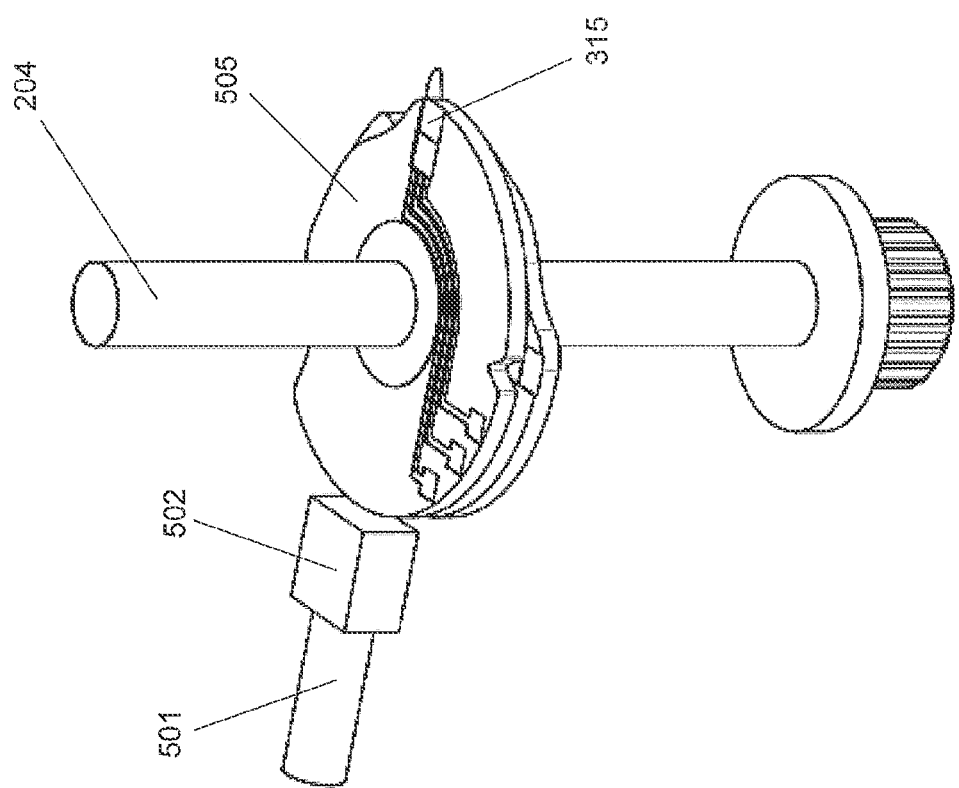

The test disc member 505 can be rotated by the drive wheel 201 and the drive belt 202 such that the blood collection part 315 is aligned with the cartridge aperture 104, which position is shown in FIG. 9. This may be done immediately after the lancing or only after the microprocessor 212 has determined that a predetermined quantity of blood has been expressed. The plunger arrangement 500 may then be activated again so as to displace the test disc member 505 radially. This causes the blood collecting portion 315 to be moved into the cartridge aperture 104. Due to the elongate shape of the cartridge aperture 104, the test disc member 505 is able to protrude from the cartridge 106 such that the blood collection part 315 enters the aperture 105 in the outer housing 107. This brings the blood collection part 315 into contact or close proximity with the user's digit, allowing a blood sample to be absorbed.

In some embodiments, a second cutaway portion may be provided on the other side of the blood collection part 315 from the first cutaway portion 302. The resulting shape of the test disc member 505 in this region allows the blood collection part 315 to protrude further from the cartridge 106. Alternatively or in addition, the test disc member 505 may have a degree of compressibility and the plunger arrangement 500 may be configured to exert sufficient force to compress the test disc member 505 against the inner wall of the cartridge 106 in order to increase the degree of radial displacement of the test disc member 505.

In any case the plunger arrangement 500 is configured to displace the test disc member radially and to maintain it in this position for a predetermined length of time (e.g. 5 to 20 seconds) sufficient for a blood sample to be absorbed into the blood collection part 315. The blood sample is drawn through the blood collection part 315 into the blood analyte measuring part 316. After the predetermined length of time, force is removed by the plunger arrangement 500 allowing the annular centre portion 508 to return to its original form, through elastic reformation.

Figure 10:
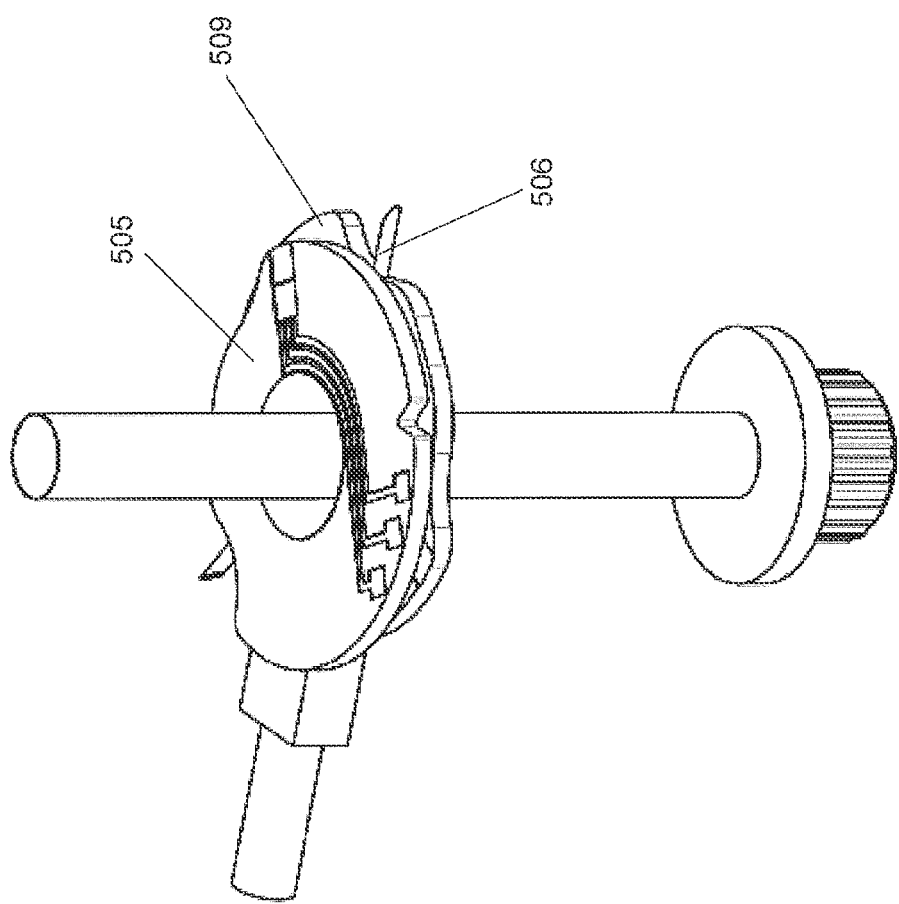

A measuring circuit connected to the analyte measuring part 316 by way of the conductive tracks 317 and the contact pads 318 then is able to determine a blood glucose level of the user. After a measurement of blood glucose level is taken, the test disc member 505 is rotated further anticlockwise so that the second guide member 206 is aligned with the notch 301. At this point the first guide member 205 is coincident with the cutaway portion 302 and thus the test disc member 505 is allowed to move upwards within the cartridge 106. As a result, the test disc member 509 that is immediately below the first test disc member 505 also moves upwards within the cartridge 106 and is provided to be coincident with the aperture 104, the slit aperture 400 and the plunger aperture (not shown). Subsequent application of a plunging force by the plunger arrangement 500 causes a lancet 506 of the second test disc member 509 to be forced out of the aperture 104, as is shown in FIG. 10. The process can be repeated for other test disc members included in the cartridge 106.

By providing a stack of test disc members within the cartridge 106 and by providing a suitable physical arrangement, a cartridge 106 can be used for multiple tests. When the cartridge 106 is new, the test disc members are located in the bottom half of the cartridge 106, with the uppermost test disc member being aligned with the aperture 104. As test disc members are used, the stack of test disc members moves upwards in the cartridge. When the last test disc member is used, the cartridge can be said to be spent. At this stage, all of the test disc members are located in the uppermost portion of the cartridge 106.

It will be appreciated that the number of test disc members that can be accommodated within the cartridge 106, and thus the number of tests that can be provided by a cartridge 106, is a factor of the height of the cartridge 106 and the separation between corresponding parts (e.g. the upper surfaces) of adjacent test disc members. A taller cartridge and/or a reduced separation of test disc members increases the number of tests that can be performed using a single cartridge 106.

An advantage of the arrangement shown in FIGS. 5 to 10 is that a rotational arrangement can be used whilst allowing the lancet 506 to penetrate a user's skin in a longitudinal direction with respect to the lancet 506. Another advantage is that puncture can occur at any desired location, for instance on the end of the user's digit.

The convenient size of the BGM 100 and the automation of the lancing and blood collecting steps means that the device 100 can be operated with one hand by a user.

Another advantage is that the arrangement can allow the penetration depth of the lancet 506 to be easily predictable. Furthermore, it allows the penetration or puncturing depth to be adjustable. In particular, the adjustment of the penetration depth can be achieved by a mechanical arrangement that limits movement of the plunger arrangement towards the shaft 204. Alternatively, it can be achieved in an electromechanical manner by measuring the location or displacement of some part of the mechanism and ceasing applying an energising voltage to a solenoid or other transducer that is used to affect movement of the plunger arrangement 500. The penetration depth may be specified by a user. The depth may be specified by a user and may be achieved through software or firmware control of rotation of the shaft 204. The value defining the depth may be stored in memory. Penetration depth control is important to many users since lancet penetration usually is painful and since penetration depth control allows users some control over their experience. The device may also allow the user to set and adjust the penetration speed. The speed of the lancing may also affect the amount of pain felt by a user.

In FIG. 11 the hollow cylindrical housing part 203 is shown with the aperture 104 and the shaft 204 located as described above. A slit aperture 400 is provided in the hollow cylindrical housing part 203. The slit aperture 400 is located at substantially the same height as the aperture 104. However, the slit aperture 400 is located on a side of the hollow cylindrical housing part 203 that is substantially opposite the aperture 104.

The slit aperture 400 is not visible when the cartridge 106 is in place within the BGM 100.

Adjacent to the slit aperture 400 is located a swing arm 401. The swing arm 401 is rotatable about a spindle 402. The spindle 402 has an axis that is parallel to the axis of the shaft 204. The axis of the spindle 402 is located above the drive belt 202. A connecting arm (not visible) connects the spindle 402 to the swing arm 401. In this example, the connecting arm is connected to the swing arm 401 by a vertical connector 404. The vertical connector 404 allows the spindle 402 on which the connecting arm is mounted to be located at a different vertical position to the swing arm 401. The spindle 402, the connecting arm and the vertical connector 404 are arranged such that when the connecting arm is rotated on the axis of the spindle 402 the swing arm 401 is moved towards the shaft. The movement of the swing arm 401 is substantially radial with respect to the shaft 204.

Mounted on the swing arm 401 are first to third electrical contact terminals 405. Each includes a generally horizontal arm and a depending contact head. The electrical contact terminals 405 are made of a resilient conductive material, for instance metal. The depending contact heads are angled at their ends furthest from the swing arm 401.

In one position, shown in FIG. 11, the electrical contact terminals 405 are supported by the swing arm 401 such that the dependent contact heads are located within the slit aperture 400 or alternatively outside of the hollow cylindrical housing part 203. After the test disc member 505 has been rotated such that the blood collection part 315 is coincident with the aperture 104, and the blood sample has been collected via action of the plunger arrangement 500, the contact pads 318 are coincident/aligned with the slit aperture 400. As the test disc member 505 is held in this position, the connecting arm is caused to rotate around the axis of the spindle 402 such that the swing arm 401 moves towards the shaft 204. The arrangement is such that the depending contact heads of the electrical contact terminals 405, but not the horizontal arms, come into contact with the contact pads 318 as the electrical contact terminals 405 move into the volume above the upper surface 303 of the test disc member 505. The resilient properties of the electrical contact terminals 405 causes the electrical contact terminals to be forced against the contact pads 318. As such, an electrical connection is provided between the horizontal arms of the electrical contact terminals 405 and the analyte measuring part 316. Electronic measuring means (not shown) connected to the electrical contact terminals 405 operate to pass a voltage through the contact terminals 405 and the analyte measuring part 316 and to take measurements of electrical parameters, from which a measurement of an analyte concentration level, for example a blood glucose level, can be determined.

The connecting arm is controlled to remain in this position for a predetermined time or alternatively until it is detected that a blood glucose level measurement has been made, after which the connecting arm is caused to rotate around the shaft 402 so as to remove the electrical contact terminals 405 from the position above the upper surface of the test disc member 505. Once the electrical contact terminals 405 have been retracted, the test disc member 505 is rotated anticlockwise so as to allow the test disc members to move upwards on the shaft 204.

It will be appreciated that the maximum permissible height dimension of the electrical contact terminals 405 is determined by the height of the spacer member which separates adjacent test disc members. A thicker spacer member allows larger electrical contact terminals 405 to be used. However, this is at the expense of an increase in separation between adjacent test disc members, and thus a reduced capacity for the cartridge 106. The use of electrical contact terminals 405 including a horizontal arm and a depending contact head allows the height dimension of the electrical contact terminals to be minimised whilst allowing good electrical contact between the electrical contact terminals and the contact pads 318 and also allowing the electrical contact terminals 405 to operate correctly over a sufficient number of cycles.

Figure 12:
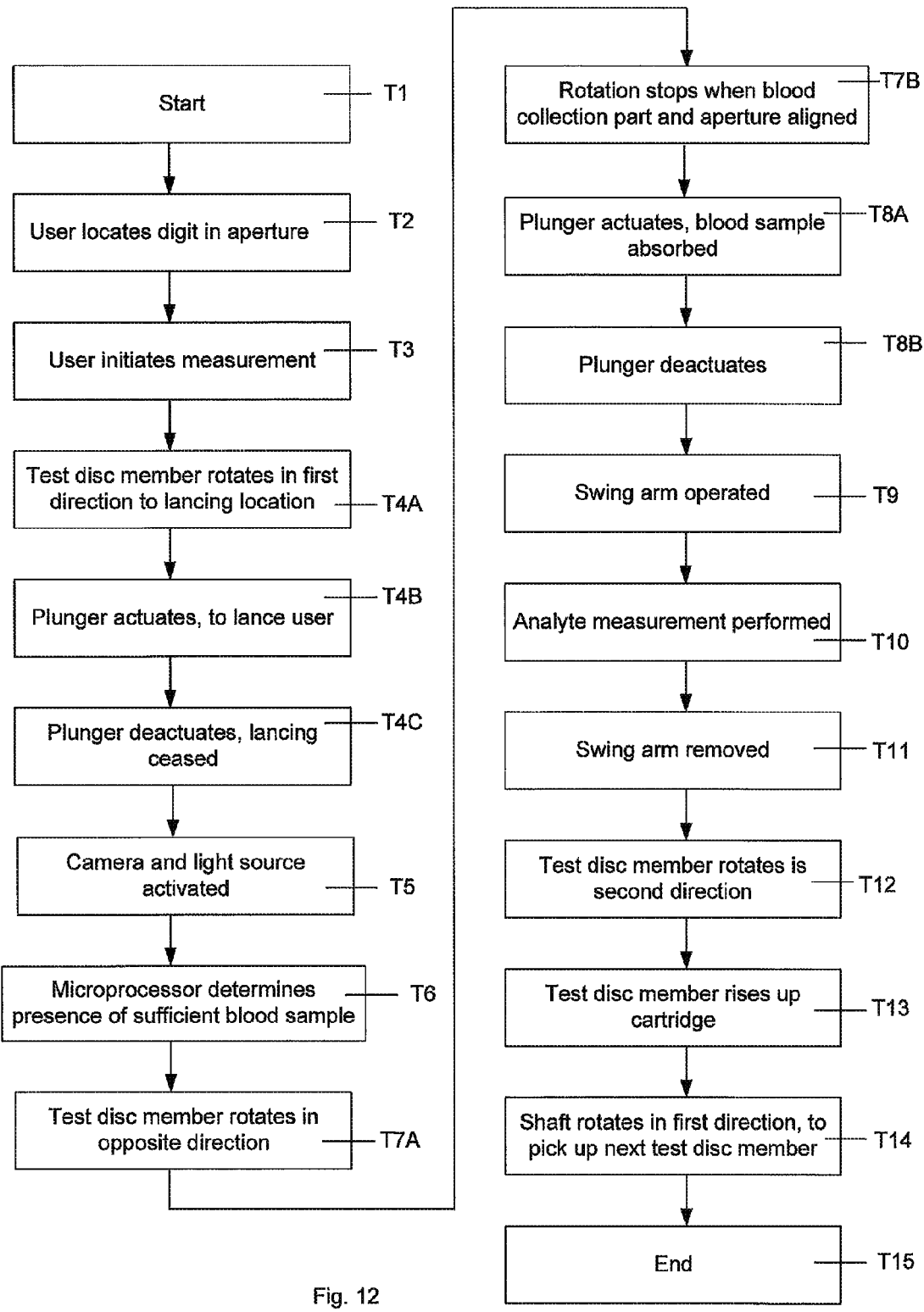
FIG. 12 is a flowchart illustrating operation of the BGM of FIG. 1.

Operation of the blood glucose meter 100 will now be described with reference to the flowchart of FIG. 12.

Operation starts at step T1. At step T2, the user locates their digit in or against the aperture 105. At step T3, the user initiates blood glucose measurement. This may involve the user operating an input key or switch (not shown) on the device 100. This is detected by the microprocessor 212. The software/firmware stored in the ROM 214 uses the input to call a function or to execute a software module. The software/firmware stored in the ROM 214 then causes the microprocessor 212 to issue a command to a motor attached to the drive wheel 201 through the motor interface 217 to rotate the shaft 204 in a clockwise direction. The software/firmware controls the extent of the rotation.

Following step T3, the microprocessor 212, under control of the software/firmware stored in the ROM 214, causes the shaft 204 to be rotated by a motor through the motor interface 217 and to cease rotation once the lancet 506 is aligned with the apertures 104, 105, and thus is aligned with the user's digit, at step T4A. At step T4B, the microprocessor 212, under control of the software/firmware stored in the ROM 214, causes actuation of the plunger arrangement 500, through the motor interface 217. The control of the actuation of the plunger is such as to limit the extent of movement of the lancet 506 to a predetermined extent. The predetermined extent is set by a user prior to the blood glucose measurement. In effect, the user can set a lancing depth, which is stored in a suitable way in the ROM 214 by action of the microprocessor 212, operating under control of the software/firmware stored in the ROM 214.

When the maximum extent of plunger actuation has been reached at step T4B, at step T4C the plunger arrangement 500 is deactuated by the microprocessor 212, under control of the software/firmware stored in the ROM 214, and lancing ceases. At this step, the test disc member returns to its original position by action of the elasticity of the annular centre portion 508 of the test disc member 508.

At step T5 the camera 110 and light source 216 are activated. The light source 216 illuminates the area of lancing. The camera 110 captures and relays images of the area of lancing back to the microprocessor 212. In some embodiments, one or both of the camera 110 and light source 216 may be activated prior to lancing. The microprocessor 212 then performs determinations of the quantity of blood which has been expressed from the wound. At step T6, the microprocessor 212 determines that a sufficient quantity of blood is present of the surface of the user's digit for an accurate blood glucose analysis to be performed.

The software/firmware stored in the ROM 214 then causes the microprocessor 212 to control the motor to rotate the shaft 204 in the opposite direction, at step T7A.

At step T7B, the software/firmware causes the microprocessor 212 to control the motor to cease rotation when the shaft 214 is such that the blood collection part 315 is coincident with the apertures 104, 105, and thus the user's digit.

At step T8A, the microprocessor 212, under control of the software/firmware stored in the ROM 214, causes actuation of the plunger arrangement 500, through the motor interface 217. The plunger is maintained at this position for a predetermined length of time to allow the blood to be absorbed into the blood collection part 315. At step T8B the plunger arrangement 500 is deactuated by the microprocessor 212, under control of the software/firmware stored in the ROM 214. At this step, the test disc member returns to its original position by action of the elasticity of the annular centre portion 508 of the test disc member 508

At step T9, the software/firmware controls a motor such as to cause the swing arm 401 to be rotated towards the shaft 204. The software/firmware stored in the ROM 214 is such that the microprocessor 212 causes only the required amount of travel of the swing arm 401. At this point, the analyte interface circuit 219 is coupled directly to the blood analyte measuring part 316, which by action of the blood collection part 315 has been provided with blood from the user's digit. At step T10, analyte measurement is performed. This involves the analyte interface circuit 219 providing voltages to the electrical connection contacts 318, and thus to the blood analyte measuring part 316, and measuring parameters of resulting signals. The measured parameters, particularly voltage parameters, are used by the software/firmware stored in the ROM 214, as executed by the processor 212, to calculate a blood glucose measurement level of the user. The blood glucose measurement may then be displayed on a display. At step T11, the swing arm is caused to be removed by action of the microprocessor 212, under control of the software stored in the ROM 214, the motor interface 217 and the motor (not shown).

At step T12, the software/firmware results in the microprocessor 212 controlling the drive disc 201 to rotate anti-clockwise. Rotation continues until the notch 301 on the test disc member is coincident with the guide 206. At step T13, the test disc member rises up the cartridge 106. In the case where biasing of the test discs up the cartridge 106 is provided by a bias means, for instance a spring, step T13 requires no action on part of the software/firmware and microprocessor 212, although there may be a pause before the next step. In embodiments where movement of the test disc members along the shaft 204 occurs through driving action, step T13 involves the microprocessor 212, under control of the software/firmware stored in the ROM 214, controlling a motor through the motor interface 217. Subsequently, at step T14, the microprocessor 212, under control of the software/firmware stored in the ROM 214, causes the shaft 204 to rotate again in a clockwise direction in order to engage with the next test disc member in the cartridge 106. At this stage, the test disc members rise up the cartridge 106 slightly.

The operation ends at step T15.

Various modifications and alternative features can be used in connection with the above-described embodiments. Some alternatives now follow.

Although the test disc member 505 has been described as having a lancet 506 which protrudes radially from the disc, the lancet 506 may instead protrude at an angle with respect to a radial line. Additionally, although the lancing has been described as occurring radially, where the lancet is disposed at an angle, the lancing may instead occur by rotational movement of the test disc member 505. Although the lancet 506 has been illustrated as straight, it may instead be curved for a portion or all of its length.

In addition to analysing images received from the camera 110 to determine whether a sufficient quantity of blood is present, the microprocessor 212 may also be configured to analyse images of the user's digit when placed against the aperture 105. From this analysis, the microprocessor 212 is able to determine whether the user's digit is present in the aperture 105. This allows the process of lancing and blood collection to begin automatically. This analysis may also allow the microprocessor 212 to determine whether the user's digit is located in the optimal position for lancing. In order to produce a good contrast between the user's digit, which may have a one of a range of skin tones depending on the user, and the inner surfaces of the BGM 100, the inside of the BGM may be painted or otherwise coloured green. This contrast allows the microprocessor 212 to determine the silhouette of the user's digit and/or to subtract the background of the image.

In some further embodiments, the BGM 100 may additionally comprise a speaker and may be configured to issue pre-recorded voice commands to a user to encourage correct placement of their digit in the aperture 105. For example, when the device 100 is ready to perform a blood collection operation a command "present finger to sampling area" may be issued. Once presented, if the user's digit is not protruding far enough into the aperture 105, as determined by the microprocessor 212 from the received images, a command such as "press harder" may be issued. After lancing and when the blood collection part 315 is presented to the user's digit, a command such as "please wait" may be issued.

The camera 110 may additionally be used as a blood analysis tool. For instance, the colour of the blood expressed from the lancet puncture may be analysed to determine haemoglobin and/or oxygenation levels. In particular the brightness and hue of the blood are indicative of these properties. These properties may be measured by the microprocessor 212 directly from the images received from the camera 110.

It has been described that the penetration depth of the lancet 506 is settable by the user. However, the actual penetration depth may vary depending on the precise position of the user's digit. With a suitable field of view, the camera 110 is able to capture images of the lancet 506 and determine its position. Positional indicators may be provided on the lancet 506 and/or on the test disc member 505 to aid in this determination. The microprocessor 212 may use these "live" images of the position of the lancet 506 to control and adjust the movement of the lancet (via the plunger arrangement 500) and hence the resulting penetration depth.

Instead of the blood collection part 315 being located next to the third position 314, i.e. bounding only the part of the disc edge 305 that is purely circumferential, the blood collection part could instead be located on the disc edge 305 at the junction between the cutaway portion 302 and the circumferential portion. The blood collection 315 part in this instance may extend for between 0.5 mm and 2 mm along the disc edge 305 at the cutaway portion 302. The blood collection 315 part in this instance may also extend for between 0.5 mm and 2 mm along the disc edge 305 at the circumferential part.

Alternatively or additionally, the analyte measuring part 316 may be sandwiched between two layers of wicking material, the wicking material causing the blood to be drawn through the analyte measuring part 316.

Although in the above the shaft 204 is said to be driven by a drive wheel 201 that is coupled to the shaft 204 by a drive belt 202, the drive may instead be direct (i.e. the drive mechanism is coupled directly to the shaft 204), or connection may be made by a notched belt, a vee belt, or by a direct gear mechanism. Instead of an electric motor, a clockwork drive could be used. A clockwork drive mechanism has a number of advantages, particularly where access to batteries or battery chargers or electricity supplies are limited. In the embodiments in which a clockwork mechanism is used, the user can be sure that the BGM 100 will not cease operating because of drained batteries. A clockwork mechanism may be particularly suited to developing countries and emerging markets.

In embodiments in which an electrical motor is used to drive the shaft 204, preferably control is exerted over the motor by software. In this way, the speed of rotation can easily be controlled. Additionally, the extent of rotation can more easily be controlled. The motor may be a stepper motor.

Alternatively, a mechanical drive arrangement may be present, for instance using a lever or other device for manual actuation. A suitable mechanism may be one similar to those previously used in SLR cameras.

The swing arm 401 may be actuated in any suitable way. For instance, it may be driven by the same motor or mechanism as the shaft 204. Alternatively, it may be driven by a separate motor. In either case, the rotation of the swing arm 404 may be affected by a cam mechanism, or by a pin and slot (track path) mechanism. In the event of an electric motor being used, the motor preferably is software driven. The motor preferably is a stepper motor.

The mechanical arrangement may include a mechanism by which a bias means, for instance a mechanical compression spring, is biased and then released in order to push the electrical contact terminals 405 into place. The terminals 405 can then be refracted by the swing arm 401 using a rotating motion. The overall mechanism can be termed a latch type trigger mechanism.

Instead of a swing arm 401 being used to rotate the electrical contact terminals 405 into place, the contact pads 318 may instead be located on the disc edge 305, allowing the use of fixed electrical contact terminals 405. The electrical contact terminals may include a brush or other deformable feature such that the test disc members can move whilst in contact with the electrical contact terminals without damage occurring to any of the components. Similar arrangements are used in brushed DC motors. In this case the electrical contact terminals 405 could be flexible finger contacts that rest on the periphery of the test disc members in order to contact the contact pads 308.

Alternatively, instead of a swing arm 401, a mechanism may be used to affect longitudinal movement of the electrical contact terminals 405 into place to contact the contact pads 318.

The conductive tracks 317 and the contact pads 318 may be formed by leadframe. Alternatively, overmoulding may be used. Alternatively, printed circuit board (PCB) printing may be used.

Optionally, each of the test disc members is separated from adjacent test disc members by a membrane (not shown in the drawings). In this case, the membrane preferably fits closely to the internal surface of the hollow cylindrical housing part 203. An effect of the membrane is to reduce the possibility of disc cross-contamination. Use of a membrane may allow the test disc members to have a reduced separation than would be the case without the use of a membrane.

In the above, the test disc members 505 are said to be biased upwards by a bias means, for instance a compression spring. Alternative mechanisms for moving the test disc members 505 up the cartridge may be used. For instance, a threaded lifting cam may be provided on the shaft 204 or alternatively on the interior surface of the hollow cylindrical housing part 203.

Instead of the blood collection part 315 wicking blood towards the analyte measuring part 316, blood may be communicated to the analyte measuring part 316 instead through gravity.

Additionally, the test disc members 505 may include a disinfecting or cleaning portion that contacts the digit before lancing. This can reduce risk of infection of the wound and also can increase accuracy in particular by removing any glucose from the skin (as may occur after eating fruit etc.). In addition, some blood glucose measuring technologies require the first drop of blood to be removed in order to produce an accurate result.

Additionally or alternatively, the test disc members 505 may include a cleaning portion that is arranged to contact the digit subsequent to the blood collection part 305. This can remove additional blood from the finger, and may also serve to assist closure of the puncture.

The invention claimed is:

1. Apparatus for detecting presence of a blood sample, the apparatus comprising:
a housing having an aperture, the aperture configured to receive a body part of a user, wherein the housing is configured to retain a cylindrical cartridge having a vertical axis that is coaxial with an elongate shaft supported centrally within the cylindrical cartridge, where the elongate shaft is rotatable and has directly mounted thereon a plurality of testing members, wherein each of the plurality of testing members include a notch at a first position at an edge of each of the plurality of testing members and a cutaway portion at a second position at the edge of each of the plurality of testing members, and wherein each of the plurality of testing members rotates with the shaft and comprises a blood collection part located at a third position at the edge of each of the plurality of testing members, wherein the third position is located between the notch and the cutaway portion;
a camera having a field of view that encompasses at least a portion of the aperture, the camera configured to capture images of the user's body part; and
a processor configured to:
control operation of the camera;
receive the captured images;
determine whether a predetermined quantity of blood is present on the surface of the user's body part.

2. Apparatus according to claim 1, further comprising a lancet protruding from a the cutaway portion of each of the plurality of testing members, wherein indicators are provided on the lancet.

3. Apparatus according to claim 1, wherein the camera is mounted on or within the housing.

4. Apparatus according to claim 2, wherein the camera is mounted on or within the cartridge.

5. Apparatus according to claim 1, wherein the processor is further configured, in response to a positive determination that a predetermined quantity of blood is present on the surface of the user's body part, to control the apparatus to present the blood collection part of a first one of the plurality of testing members to the aperture.

6. Apparatus according to claim 1, wherein each of the plurality of testing members are moveable along the cartridge such that different ones of the testing members are able to be presented at the aperture in turn.

7. Apparatus according to claim 1, wherein the processor is further configured to analyse the captured images to detect a position of the user's body part.

8. Apparatus according to claim 1, wherein the processor is further configured, in response to a detection that the user's body part is within a range of predetermined positions, to control the apparatus to advance the lancet of a first one of the plurality of testing members into the aperture, thereby to lance the user's body part.

9. Apparatus according to claim 1, the apparatus further comprising a light source configured to illuminate the user's body part.

10. Apparatus according to claim 1, wherein the processor is further configured to analyse the captured images to measure a property of the blood sample.

11. Apparatus according to claim 1, wherein the aperture is configured such that a portion of the body part of the user enters the aperture.

12. A method of detecting presence of a blood sample, the method comprising:

providing a housing having an aperture, the aperture configured to receive a body part of a user, wherein the housing is configured to retain a cylindrical cartridge having a vertical axis that is coaxial with an elongate shaft supported centrally within the cylindrical cartridge, where the elongate shaft is rotatable and has directly mounted thereon a plurality of testing members, wherein each of the plurality of testing members include a notch at a first position at an edge of each of the plurality of testing members and a cutaway portion at a second position at the edge of each of the plurality of testing members, and wherein each of the plurality of testing members rotates with the shaft and comprises a blood collection part located at a third position at the edge of each of the plurality of testing members, wherein the third position is located between the notch and the cutaway portion;

providing a camera having a field of view that encompasses at least a portion of the aperture, the camera configured to capture images of the user's body part; and providing a processor configured to:
control operation of the camera;
receive the captured images;
determine whether a predetermined quantity of blood is present on the surface of the user's body part.

* * * * *